United States Patent [19]

Fleischhacker, Jr.

[11] Patent Number: 5,069,217

[45] Date of Patent: Dec. 3, 1991

[54] STEERABLE GUIDE WIRE

[75] Inventor: Joseph F. Fleischhacker, Jr., Mound, Minn.

[73] Assignee: Lake Region Manufacturing Co., Inc., Chaska, Minn.

[21] Appl. No.: 549,740

[22] Filed: Jul. 9, 1990

[51] Int. Cl.$^5$ ............................................. A61B 6/00
[52] U.S. Cl. .................................. 128/657; 128/772; 604/170; 604/280; 604/282
[58] Field of Search .................. 128/657, 772; 604/9, 604/167, 170, 286, 282

[56] References Cited

U.S. PATENT DOCUMENTS

| | | | |
|---|---|---|---|
| 3,906,938 | 9/1975 | Fleischhacker | 128/2 |
| 4,516,972 | 5/1985 | Samson | 604/282 |
| 4,538,622 | 9/1985 | Samson et al. | 128/772 |
| 4,545,390 | 10/1985 | Leary | 128/772 |
| 4,554,929 | 11/1985 | Samson et al. | 128/772 |
| 4,724,846 | 2/1988 | Evans | 128/657 |
| 4,763,647 | 8/1988 | Gambale | 128/657 |
| 4,813,434 | 3/1989 | Buchbinder | 128/657 |
| 4,815,478 | 3/1989 | Buchbinder | 128/657 |
| 4,846,186 | 7/1989 | Box et al. | |
| 4,884,579 | 12/1989 | Engleson | 128/772 |
| 4,922,924 | 5/1990 | Gambale | 128/657 |
| 4,940,062 | 7/1990 | Hampton | 128/657 |
| 4,953,553 | 9/1990 | Tremulis | 128/657 |

OTHER PUBLICATIONS

Drawing entitled "Guidewire, Coronary, Sub Ass'y, Soft Tip, Torqueable Radiopaque", dated Jan. 6, 1983.

Primary Examiner—Kyle L. Howell
Assistant Examiner—Robert L. Nasser, Jr.
Attorney, Agent, or Firm—Hugh D. Jaeger

[57] ABSTRACT

A steerable guide wire for use in a medical procedure, such as coronary angioplasty, which requires positioning a catheter or other device at a remote location within the body by way of the cardiovascular system or other passage way. The guide wire has a solid core wire which runs the entire length. The distal end of the core wire is tapered to an intermediate diameter to permit insertion into a short flexible coil, or a combination of a flat wire coil and round wire coil attach to each other at a brazed joint. The flexible coil has an outside diameter approximately equal to the outside diameter of the core wire proximal to the taper. The proximal end of the flexible coil is fixedly attached to the taper. The distal tip of the core wire is further tapered and optionally flattened to enhance the handling characteristics as well as flexibility. The distal tip of the core wire and a flexible round wire coil are coextensive, and attached distally to form a smooth tip for the guide wire. The entire guide wire can be coated with a polymer or other suitable material to control, and reduce friction over the length of the guide wire.

1 Claim, 3 Drawing Sheets

GUIDE WIRE TABLE

| Section of the Core | Length | Diameter |
|---|---|---|
| A-B | 150 cm * | .012-.018 * |
| B-C | 2 cm * | .016-.010 * |
| C-D | 5-15 cm * | Constant D * |
| D-E | 4-15 cm * | .010-.003 * |
| E-F | 2 cm * | flat cross * section of .002 - .0045 |
| A-F | 180 cm * | see above * |
| B-F | 30 cm * | see above * |

* approximate

FIG. 3

STEERABLE GUIDE WIRE

BACKGROUND OF THE INVENTION

1. Field of the Invention

The present invention relates generally to devices for use in medical procedures, and more particularly, relates to guide wires for directing a catheter or other medical device through the cardiovascular system or other passage way in the human body.

2. Description of the Prior Art

Guide wires for positioning various medical devices within the body have been known for some time. A common current application for guide wire is in percutaneous translumenal coronary angioplasty (PTCA). In this procedure, it is often necessary to steer a guide wire from an entry point in the arterial system, such as the femoral artery, to the site of occlusion of a coronary artery. A dilatation catheter can then be easily advanced over the guide wire to the treatment site.

In PTCA applications, it is necessary that the guide wire have a small diameter, be flexible enough to negotiate the tortuous arterial pathways without danger of perforation, and have sufficient steerability to permit the attending physician to select the desired pathway from a number of alternatives as branches in the arterial system are encountered. The ideal guide wire must have a flexible and bendable tip, along with the ability to evenly transmit torque from the proximal end to the distal end.

U.S. Pat. No. 4,545,390, issued to Leary shows a typical design of a guide wire for PTCA applications. In the Leary guide wire, the central core wire terminates short of the distal tip. The result is that the guide wire will tend to bow at the distal tip upon application of longitudinal force. U.S. Pat. No. 4,763,647, issued to Gambale, shows a similar design with an even shorter central core wire.

SUMMARY OF THE INVENTION

The general purpose of the present invention overcomes the problems found in the prior art by providing a small diameter guide wire, which is flexible yet steerable while providing greater safety and the desired trackability. These features are obtained through the use of a solid core wire which extends the entire length of the guide wire. Near the distal end, the core wire has a first taper from the main diameter to an intermediate lesser diameter. At the distal tip, the core wire has a second taper from the intermediate lesser diameter to the smaller distal diameter. Optionally, the distal tip of the core wire may be flattened to enhance the flexibility.

A short coil spring, having an outside diameter approximating the main diameter and an inside diameter longer than the intermediate diameter, is positioned over the distal end of the core wire. The coil spring is fixedly attached at its proximal end to the first taper of the core wire. The length of the coil spring is chosen such that when attached at its proximal end, it is coextensive with the distal tip of the core wire. The distal tips of the coil spring and the core wire are welded together to form a smooth hemispherical tip for the guide wire.

The entire guide wire may be coated with a polymer or other flexible coating. The proximal end of the guide wire is configured to correspond to the particular application. For PTCA use, the proximal end permits insertion of the dilation catheter after the guide wire has been properly positioned.

BRIEF DESCRIPTION OF THE DRAWINGS

Other objects of the present invention and many of the attendant advantages of the present invention will be readily appreciated a the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
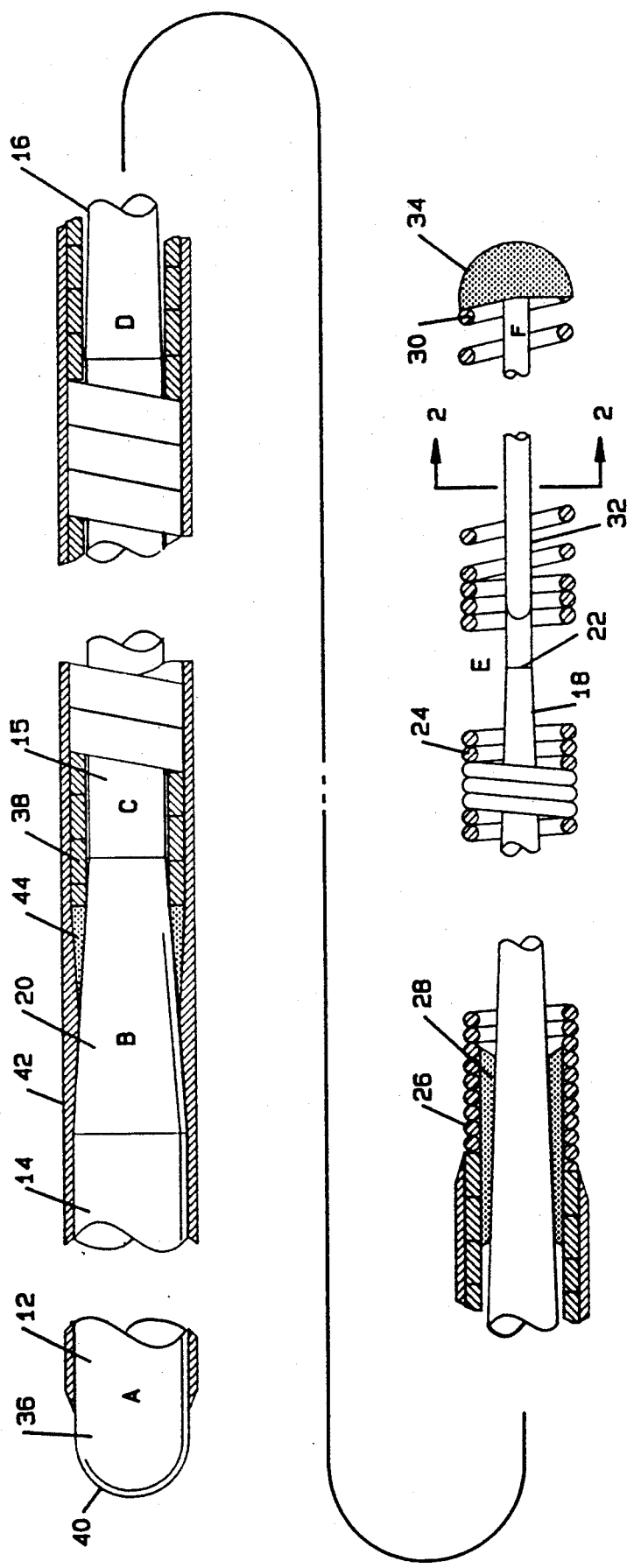
FIG. 1 illustrates a partially sectioned plan view of a guide wire, the present invention.

FIG. 1 is a plan view of a guide wire 10 incorporating the present invention, which has been partially sectioned to show the details of the construction and the operation. The inner element of guide wire 10 is a core wire 12 which is preferably a solid wire of 304 stainless steel or other similar material suitable for acute use in the human body. It is approximately 180 cm. in length between points A to F for PTCA applications by way of example and for purposes of illustration only, and not to be construed as limiting of the present invention. Core wire 12 may have proximal end 36 configured as is appropriate for the application such as hemispherical proximal end 40 in a diameter range of 0.012 to 0.018 inches.

The main body of core wire 12 is approximately 150 cm length between points A to B of a total length of 180 cm, and has a constant main diameter 14 of about 0.12–0.018 inch. From the main body diameter 14, the diameter 20 next first tapers over about 2 cm distance between points B-C. An intermediate diameter 15 is substantially constant between points C-D. The diameter 16 further secondly tapers over a 4-15 cm distance from points D-E. The final diameter optionally resembles the cross section of FIG. 2 over a distance of about 2 cm between points E-F. The distance between points B-F is about 30 cm. Beginning about 5-15 cm from the distal tip of core wire 12, the diameter tapers along distance 16 to the smallest distal diameter 22 of about 0.003 inch. Optionally and preferably, the most distal 2 cm of core wire 12 between points E-F may be flattened at 32 to reduce the stiffness and achieve greater flexibility.

A flat wire coil 38 can be in intimate contact with the first tapered diameter 20 and is brazed to the core wire at each end at 28 and 44.

A flexible coil spring 24 attaches to about the most distal 5 cm of core wire 12. The flexible coil spring 24 has an outside diameter of about 0.012 to 0.018 inch and an inside diameter of about 0.010–0.012 inch. The most proximal portion 26 of coil spring 24 is tightly wound, and attaches to the core wire 12 by the brazed joint 28. The most distal portion 30 of the coil spring 24 is more loosely wound to improve the flexibility of the distal tip. At the distal end, coil spring 24 and core wire 12 are coextensive. These two components are fixedly attached by the hemispherical weld 34 which provides a smooth distal tip for insertion and maneuvering of the guide wire 10.

The main body of core wire 12 along main diameter 14 may be optionally covered with a polymer 42 to improve handling characteristics. In the preferred embodiment, this is a polymer coating of PTFE, MDX, or any other suitable coating of about 0.0005 inch. Optionally the most distal 4 cm may be left uncoated as illustrated. Preferably, the most proximal end of 2-3 cm is also left uncoated as illustrated in the figure.

Figure 2:
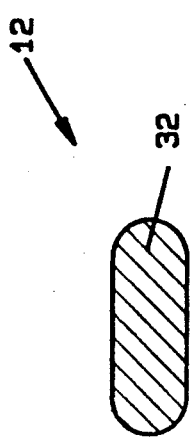
FIG. 2 illustrates a cross sectional view of the distal end of the core wire as optionally flattened; and, FIG. 3 illustrates a table of sections, lengths and diameters of the core wire of the guide wire.

FIG. 2 is a cross sectional view of the distal tip of core wire 12 as optionally flattened along length 32. Such flattening of core wire 12 provides increased flexibility. After flattening, core wire 12 along length 32 has cross sectional dimensions of about 0.002 by 0.0045 inch. The coil 24 is also made of radiopaque material.

FIG. 3 illustrates a table for the diameter and the length for each section of the guide wire 10.

MODE OF OPERATION

The guide wire 10 of the present invention is utilized in medical procedures in accordance with generally accepted medical practices.

Having thus described the preferred embodiments of the present invention, those of skill in the art will be readily able to apply the teachings found herein to other embodiments within the scope of the claims hereto attached.

I claim:
1. A guidewire comprising:
   a. a core wire of about 180 cm in length including in order a main diameter of about 0.012 to 0.018 inches of about 150 cm in length, a first taper of about 2 cm in length, an intermediate diameter of about 10-22 cm in length, a second taper of about 4-15 cm in length, and a final diameter of about 0.003 inches of about 2 cm in length flattened to about 0.002 inches by about 0.0045 inches;
   b. a flat wire coil brazed to said first taper and said second taper and about said core wire; and,
   c. a flexible coil spring of radiopaque material, of about 0.012 to 0.018 inches outside diameter to about 0.010 to 0.012 inches inside diameter, attached between a hemispherical weld tip and said flat wire coil brazed at said second taper and about said core wire, whereby said final diameter of said core wire and said flexible coil spring provide for insertion, flexibility and maneuvering of said guidewire with flexibility and bendability of a distal end.

* * * * *